United States Patent
Jackson, III

(10) Patent No.: US 11,000,291 B2
(45) Date of Patent: *May 11, 2021

(54) ILLUMINATED PROBE WITH REPLACEABLE TIP

(71) Applicant: OPTICAL SPINE, LLC, Grand Blanc, MI (US)

(72) Inventor: Avery M. Jackson, III, Grand Blanc, MI (US)

(73) Assignee: OPTICAL SPINE, LLC, Grand Blanc, MI (US)

( * ) Notice: Subject to any disclaimer, the term of this patent is extended or adjusted under 35 U.S.C. 154(b) by 126 days.

This patent is subject to a terminal disclaimer.

(21) Appl. No.: 15/805,524

(22) Filed: Nov. 7, 2017

(65) Prior Publication Data

US 2018/0064450 A1 Mar. 8, 2018

Related U.S. Application Data

(63) Continuation of application No. 13/728,987, filed on Dec. 27, 2012, now abandoned.
(Continued)

(51) Int. Cl.
*A61B 1/015* (2006.01)
*A61B 1/04* (2006.01)
(Continued)

(52) U.S. Cl.
CPC ...... *A61B 17/1604* (2013.01); *A61B 1/00045* (2013.01); *A61B 1/00135* (2013.01);
(Continued)

(58) Field of Classification Search
CPC ............ A61B 17/7032; A61B 17/7037; A61B 17/7074; A61B 17/7076; A61B 17/7082;
(Continued)

(56) References Cited

U.S. PATENT DOCUMENTS 5,395,383 A 3/1995 Adams et al.
5,474,588 A 12/1995 Neubardt
(Continued)

FOREIGN PATENT DOCUMENTS

| WO | 2013172869 | 11/2013 |
|---|---|---|
| WO | 2015184131 | 12/2015 |
| WO | 2017049288 | 3/2017 |

OTHER PUBLICATIONS

Photograph of ACI tapered Reamer model TR-3 by Alberta Custom Instruments Ltd. of Edmonton, Alberta Canada. In use since approximately 1987.

*Primary Examiner* — Timothy J Neal
*Assistant Examiner* — William B Chou
(74) *Attorney, Agent, or Firm* — McNees Wallace & Nurick LLC

(57) ABSTRACT

An endoscopic probe for use during spinal surgery has an enlarged proximal end for cooperation with the hand of the surgeon and an elongate shaft terminating in a functional distal tip. The tip may be detachable for replacement. An endoscope extends through the shaft and is connected with a monitor to enable the surgeon to visually observe the area being treated. In a preferred form, a light means extends through the shaft to illuminate the area being treated, and in a further preferred form a conduit extends through the shaft to convey a fluid to flush the area being treated. In a further embodiment, two endoscopes are associated with the probe.

16 Claims, 13 Drawing Sheets

Related U.S. Application Data

(60) Provisional application No. 61/647,747, filed on May 16, 2012.

(51) Int. Cl.

| | |
|---|---|
| *A61B 1/06* | (2006.01) |
| *A61B 1/12* | (2006.01) |
| *A61B 17/16* | (2006.01) |
| *A61B 17/34* | (2006.01) |
| *A61B 1/313* | (2006.01) |
| *A61B 17/70* | (2006.01) |
| *A61B 1/00* | (2006.01) |
| *A61B 17/00* | (2006.01) |

(52) U.S. Cl.
CPC ............... *A61B 1/015* (2013.01); *A61B 1/04* (2013.01); *A61B 1/06* (2013.01); *A61B 1/3135* (2013.01); *A61B 17/00234* (2013.01); *A61B 17/1655* (2013.01); *A61B 17/3472* (2013.01); *A61B 17/7074* (2013.01); *A61B 1/126* (2013.01); *A61B 17/1615* (2013.01); *A61B 17/1671* (2013.01)

(58) Field of Classification Search
CPC . A61B 17/16; A61B 17/1615; A61B 17/1617; A61B 17/17; A61B 17/1739; A61B 17/1757; A61B 5/06
USPC ........ 600/104, 109, 117, 156–158, 160, 178, 600/182, 424; 606/79
See application file for complete search history.

(56) References Cited

U.S. PATENT DOCUMENTS

| | | |
|---|---|---|
| 5,573,537 A | 11/1996 | Rogozinski |
| 5,609,562 A | 3/1997 | Kaali |
| 5,685,820 A | 11/1997 | Riek et al. |
| 6,007,481 A | 12/1999 | Riek et al. |
| 6,387,043 B1 | 5/2002 | Yoon |
| 6,425,859 B1 | 7/2002 | Foley et al. |
| 6,527,704 B1 | 3/2003 | Chang et al. |
| 6,855,105 B2 | 2/2005 | Jackson, III |
| 7,207,949 B2 | 4/2007 | Miles et al. |
| 7,722,530 B2 | 5/2010 | Davison |
| 8,152,714 B2 | 4/2012 | Garcia-Bengochea et al. |
| 8,221,397 B2 | 7/2012 | Bleich et al. |
| 8,255,044 B2 | 8/2012 | Miles et al. |
| 8,979,767 B2 | 3/2015 | Bartol et al. |
| 9,084,550 B1 | 7/2015 | Bartol et al. |
| 2003/0013936 A1 | 1/2003 | Jackson, III |
| 2003/0171744 A1 | 9/2003 | Leung et al. |
| 2005/0090833 A1 | 4/2005 | DiPoto |
| 2006/0074445 A1 | 4/2006 | Gerber et al. |
| 2007/0005072 A1 | 1/2007 | Castillo et al. |
| 2007/0016219 A1 | 1/2007 | Levine |
| 2007/0135803 A1 | 6/2007 | Belson |
| 2007/0288026 A1 | 12/2007 | Shluzas |
| 2008/0086140 A1 | 4/2008 | Wolf |
| 2008/0183214 A1 | 7/2008 | Copp et al. |
| 2009/0163901 A1 | 6/2009 | Fisher et al. |
| 2009/0187194 A1 | 7/2009 | Hamada |
| 2009/0227851 A1 | 9/2009 | Radojicic |
| 2010/0087823 A1 | 4/2010 | Kondrashow |
| 2010/0121153 A1 | 5/2010 | To |
| 2010/0249644 A1 | 9/2010 | Miles et al. |
| 2011/0077653 A1 | 3/2011 | Haddock et al. |
| 2011/0160731 A1 | 6/2011 | Bleich et al. |
| 2011/0184235 A1 | 7/2011 | Schostek et al. |
| 2011/0313530 A1 | 12/2011 | Gharib et al. |
| 2013/0253599 A1 | 9/2013 | Gorek et al. |
| 2014/0073986 A1 | 3/2014 | Bartol et al. |
| 2014/0142420 A1 | 5/2014 | Jackson, III |
| 2015/0032022 A1 | 1/2015 | Stone et al. |
| 2015/0080755 A1 | 3/2015 | Jackson, III |
| 2015/0230749 A1 | 8/2015 | Gharib et al. |
| 2015/0342621 A1 | 12/2015 | Jackson, III |
| 2017/0238788 A1 | 8/2017 | Jackson, III |

ILLUMINATED PROBE WITH REPLACEABLE TIP

RELATED APPLICATIONS

This application is a continuation of U.S. nonprovisional patent application Ser. No. 13/728,987, filed Dec. 27, 2012, which claims the benefit of U.S. provisional patent application Ser. No. 61/647,747, filed May 16, 2012, the entire disclosures of which are incorporated in full herein by reference.

FIELD

This invention relates generally to surgical instruments. More specifically, the invention relates to a probe for use in performing surgical procedures, particularly spinal procedures such as forming holes in a vertebral pedicle in preparation for pedicle screw insertion. According to one feature of the invention, the probe incorporates at least one endoscope to enable the surgeon to see the area being treated. According to another feature, the probe has a light to illuminate the area being treated, and according to a further feature, the probe has a replaceable tip on its distal end. According to a still further feature, the probe has a channel for directing a flushing fluid to the area being treated to maintain a clear field of vision for the endoscopic camera. The probe of the invention may have any one or any combination of these features.

BACKGROUND

It is sometimes necessary to perform surgery on the spine in order to repair trauma, correct a deformity, or alleviate the effects of disease. Spinal fusion or stabilization is one procedure that may be employed to treat these conditions. According to one source, at the present time, there are approximately 30 million spine procedures performed globally each year, including approximately 400,000 cervical and lumbar fixations performed in the U.S.

Spinal fusion may be accomplished by insertion of screws into the pedicle to stabilize a spinal segment. The pedicle is a dense, stem-like structure projecting from the posterior of a vertebra, and there are two pedicles per vertebra that connect to other structures. Since the pedicle is the strongest point of attachment of the spine, significant forces can be applied to the spine without failure of the bone-to-metal connection.

To insert pedicle screws, a long, thin, metal probe is inserted through the pedicle and into the vertebral body, forming a hole for reception of the screw. Conventional pedicle probes may be straight or curved, and comprise an elongate solid metal shaft with an enlarged hand grip on the proximal end. The probe may have a shaped distal end adapted for forming a hole through the pedicle, or a separate awl or reamer may first be used to form a hole through the pedicle, and the probe then inserted into the cancellous bone of the pedicle and into the vertebral body to develop a path for the screw.

A variety of probes are known in the prior art, including the so-called gear shift pedicle probe and the Fox pedicle probe. The gear shift probe has a round head on its proximal end, whereas the Fox probe has a flat disc-shaped head on its proximal end.

Conventional modalities used to approximate or simulate screw placement are indirect, and include fluoroscopic guidance and frameless stereotactic guidance. Approximations of the pedicle and surrounding vital structures are obtained from a CT scan or MRI done prior to surgery.

Proper positioning of a conventional probe depends to an extent upon tactile feel. For instance, advancement of the probe should be smooth and consistent. A sudden plunge suggests breaking out of the pedicle laterally, and an increase in resistance indicates abutment against the pedicle or vertebral body cortex.

These conventional modalities require a steep learning curve, and improper or inaccurate manipulation of the probe and placement of the pedicle screw can result in caudal or medial penetration of the pedicle cortex and dural or neural injury.

With conventional probes, there is no direct way to confirm that the hole was made within the pedicle and that the screw will be placed completely inside the pedicle. Surrounding structures can be injured if a portion of the screw is placed outside of the pedicle. There can be nerve root injury, epidural vessel injury, or spinal fluid leakage caused by a misplaced screw. These issues can arise in the context of other probe-assisted spinal procedures as well.

Applicant's earlier U.S. Pat. No. 6,855,105, discloses an endoscopic pedicle probe having a camera at its distal end connected with an endoscopic monitor via a fiber optic bundle extending through the probe to provide the surgeon with a view of the area being treated, thus overcoming many of the shortcomings of conventional pedicle probes.

Notwithstanding the advantages of applicant's earlier pedicle probe, illumination of the area being treated would greatly enhance use of the probe. Currently, there are no pedicle probes having any means to illuminate the pedicle and surrounding region.

Additionally, the distal tip of the probe can become worn or damaged during use, rendering the whole instrument unusable or reducing its usefulness. Further, in some instances, a tip having different characteristics or functions may be desired. A replaceable tip enables this to be achieved without having to replace the entire instrument.

Further, body fluids and debris can accumulate at the area being treated, blocking or degrading the view provided by the endoscope. It would be desirable to have a means to flush these fluids and debris away from the area being treated to maintain a clear field of view for the endoscope camera.

Accordingly, there is need for a system for and method of performing surgical procedures, particularly spinal procedures such as the insertion of pedicle screws which eliminates the guesswork and error-prone modalities of the prior art. In particular, there is need for a system which provides the surgeon with direct visual confirmation during the surgical procedure that the probe is in the right position for performing the surgical procedure. Further, there is need for a probe having a removable distal tip that can be replaced when necessary or desired. Still further, there is need for a probe having means for illuminating the area being treated. Additionally, there is need for a probe having means for directing a fluid to the area being treated to remove body fluids and debris that might otherwise obscure the area.

SUMMARY

The present invention comprises a probe having means associated with it to enable the surgeon to directly confirm the location of the probe during a surgical procedure, such as a spinal procedure. For example, in some embodiments, the probe is a pedicle probe which provides the surgeon with a visual indication during a surgical procedure of the position of the probe relative to the pedicle and surrounding structure, and which, in accordance with one aspect of the invention, has means to illuminate the pedicle. In accordance with another aspect of the invention, the distal tip of the probe is replaceable and may be disposable. In a further aspect of the invention, the probe has means associated with it to flush the area being treated to wash away body fluids and debris that would otherwise obscure the field of vision.

In particular, the probe of the invention is an endoscopic probe having an elongate shaft with a reduced diameter tip on its distal end. A camera at the distal end is connected with an endoscopic monitor via a fiber optic bundle extending through the shaft, and depending upon the positioning of the camera and the lens employed, the probe of the invention affords the surgeon direct views of the area being treated, ranging from 0° to 90° relative to the longitudinal axis of the probe shaft, depending upon the positioning of the endoscope camera.

In a preferred embodiment, a light is associated with the probe for illuminating the area being treated.

In another preferred embodiment, the distal tip can be threaded or otherwise securely removably attached to the forward or distal end of the shaft so that the tip can be replaced when worn or damaged or when a tip having different characteristics is desired. For example, different tips are contemplated depending on the surgical procedure being performed. In some instances, a cap (or no tip) might be called for, such as during an exploratory procedure.

In a further preferred embodiment, means is provided on the probe for flushing the area being treated with a fluid, such as, e.g., saline, to remove body fluids and debris that might otherwise obscure the view.

In one example of the invention, a Fox probe is modified to have a hollow shaft and a small endoscope is placed in the hollow shaft, with a camera positioned at the distal end and connected via a fiber optic bundle with an endoscopic monitor to afford either a 0°, a 45°, or a 90° view, depending upon the lens employed and the positioning of the camera.

The positioning of the probe can be directly and accurately determined during surgery. In the case of placing a screw into the pedicle, there is no question as to whether the screw will be too medial, lateral, cranial, caudal, or deep. The surgeon will know if the wall of the pedicle has been breached, and to what extent. He or she can then decide to use the planned trajectory even if there is a small breach of the pedicle wall. The probe of the invention provides the surgeon with knowledge of how much of an intrusion exists, and he or she can ascertain if critical structures will be in danger from screw placement. The surgeon can also avoid parallax that may cause errors when using fluoroscopic guidance.

Further, a probe must typically be used in many spinal procedures, and the probe of the invention will not represent an additional instrument needed for these procedures. Accordingly, there will be no additional costs or equipment needed to perform such procedures.

The probe of the invention can be utilized for many surgical procedures, for example, spinal procedures in the cervical spine for lateral mass screw placement, pedicle screw placement, or trans-articular screw placement. It can be used in the thoracic, lumbar, and sacral spine for pedicle screw placement and trans-laminar screw placement, and can be used in standard open spine fusion or in minimally invasive percutaneous spine fusion.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein.

DETAILED DESCRIPTION

Figure 1:
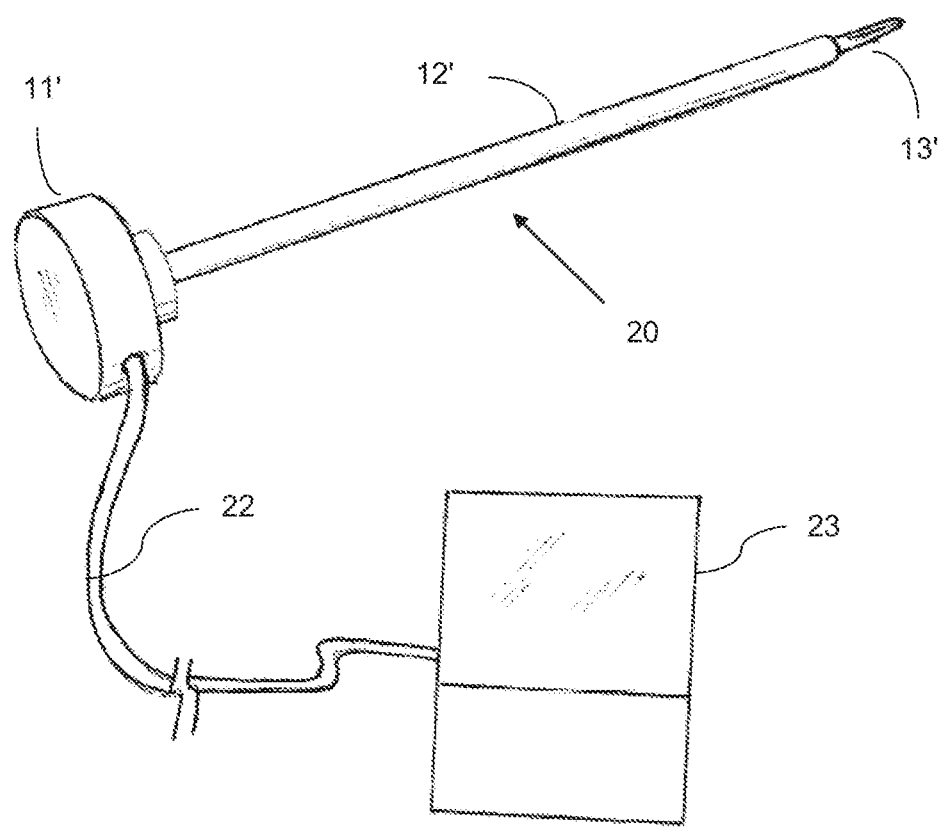
FIG. 1 is a somewhat schematic perspective view of an endoscopic pedicle probe according to the invention, in combination with an endoscopy monitor.
Figure 2:
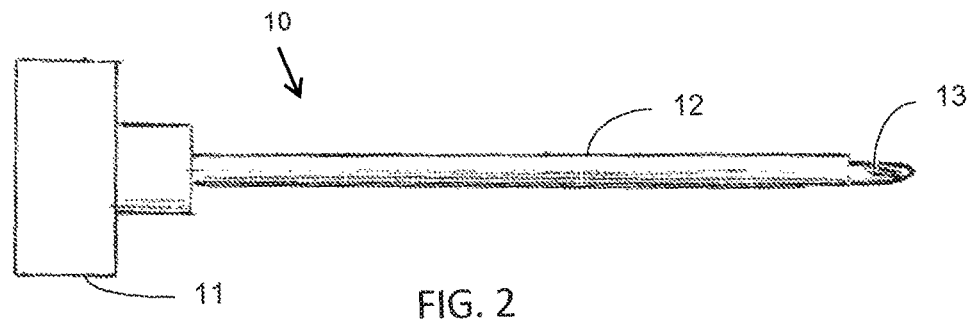
FIG. 2 is a side view in elevation of a conventional pedicle probe on which the present invention can be based.
Figure 3:
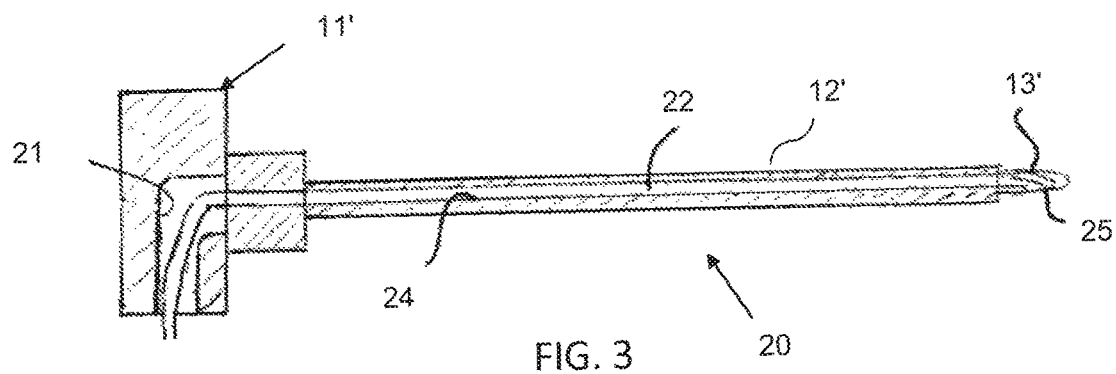
FIG. 3 is a longitudinal sectional view of a first embodiment of endoscopic pedicle probe according to the invention.

Referring more specifically to the drawings, a conventional Fox pedicle probe is depicted at 10 in FIG. 2. The probe has a disc-shaped head 11 on its proximal end that is about two inches in diameter, and a solid metal shaft 12 projecting from the center of one side thereof. A reduced diameter tip 13 on the distal end of the shaft is configured to act as a reamer, i.e., it may have a fluted configuration as found on drill bits. In use, a surgeon places the disc-shaped head 11 in the palm of his or her hand, with the shaft extending forwardly. The tip is then pushed against the pedicle while the probe is being rotated back and forth about the longitudinal axis of the shaft to form a hole in the pedicle for reception of a pedicle screw. See, for example, FIGS. 9-14.

In the specific embodiment illustrated and described herein, the pedicle probe 20 of the invention, as shown in FIGS. 1 and 3-15, is based on the Fox pedicle probe of FIG. 2. However, it should be understood that the probe 20 could be based on other commercially available probes, or could embody a completely new design. For instance, the general inventive concepts contemplate probes that could have different functional tips and, in some cases, no functional tip. The disc-shaped head 11' of the probe 20 has an opening 21 formed in it for receipt of a fiber optic cable or endoscope 22, which is connected with a suitable conventional monitor 23. Similarly, the shaft 12' has a bore 24 formed through its length for receipt of the fiber optic cable or endoscope 22, which terminates in the tip 13' at a lens 25. As in conventional pedicle probes, such as the Fox pedicle probe, the tip 13' is adapted to penetrate the hard, bony tissue of a vertebral pedicle to form a hole for reception of a pedicle screw.

As shown in the drawings, the tip has a substantially uniform diameter through a portion of its length, and terminates in a sharpened point. The diameter of the tip is approximately the same as, or slightly smaller than, the diameter of a pedicle screw to be inserted in the hole formed with the probe, and will form an elongate hole having a uniform diameter for secure engagement with a screw inserted in the hole. The tip has a hardness and configuration to act as a reamer, and preferably has a fluted configuration as incorporated, for example, in a conventional Fox pedicle probe, to facilitate penetration of the probe through the hard, bony tissue. As noted above, in some instances, the probe may be used to perform a surgical function other than formation of a hole, such as irrigating or exploring an area to be operated on.

Figure 4:
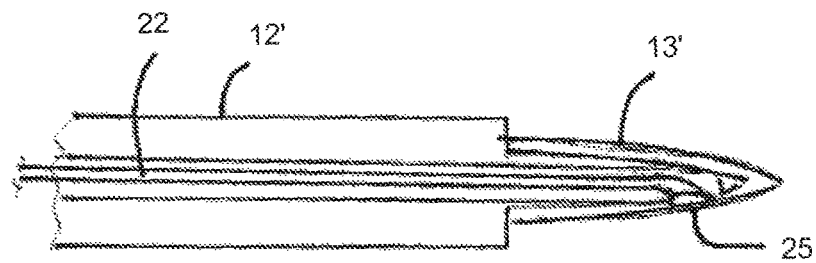
FIG. 4 is an enlarged, fragmentary, longitudinal sectional view of the distal end of the endoscopic pedicle probe of FIG. 3, depicting a 90° lens orientation.
Figure 5:
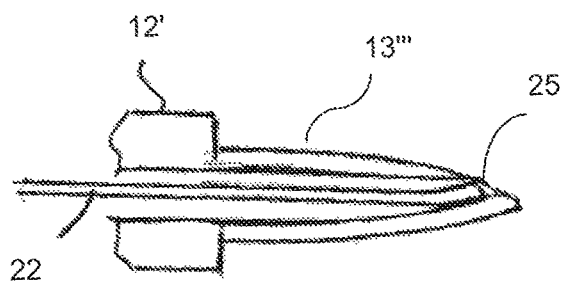
FIG. 5 is a view similar to FIG. 4, but showing a 45° lens orientation.
Figure 6:
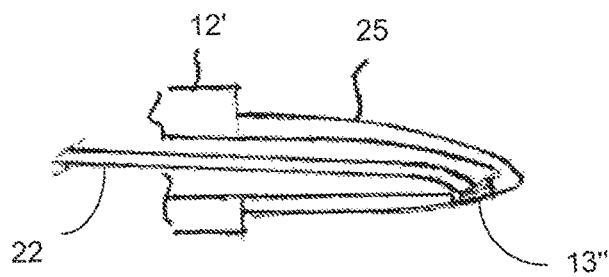
FIG. 6 is a view similar to FIG. 5, but showing a 0° lens orientation.

As shown in FIGS. 4, 5, and 6, respectively, the tip 13' or 13" or 13''' can be configured to position the lens 25 for providing a 90° view (FIG. 4), or a 45° forward view (FIG. 5), or a 0° view straight ahead (FIG. 6). Thus, for a purely exploratory procedure, the tip could simply be the means to house and position the particular lens or lenses appropriate for the procedure. Accordingly, by selection of an appropriate probe, or by appropriate manipulation of a probe, the surgeon can obtain a direct visual indication of the exact position of the probe in the area of interest (e.g., the pedicle itself and surrounding structure). As depicted in these figures, the lens is placed rearwardly of the distal point of the end to protect it when the probe is pressed against and pushed through hard bony tissue. An obturator, not shown, may be provided to close the opening through the side of the tip and protect the lens 25.

Figure 15:
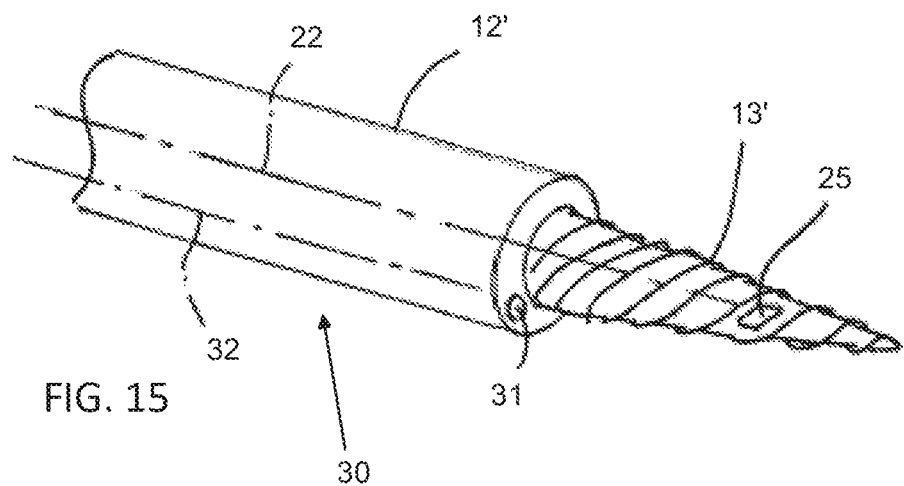
FIG. 15 is an enlarged fragmentary isometric view of the distal end of one embodiment of pedicle probe according to the invention, showing light means for illuminating the pedicle.

A second embodiment of probe 30 is shown in FIG. 15. In this modification, a suitable light 31 is placed at the distal end of the shaft 12' adjacent the base end of the tip 13'. The light 31 is connected via fiber optics 32 or other suitable means extended through the shaft 12' and connected with a suitable light source (not shown) external of the probe, and may be positioned to face axially forwardly of the shaft, as shown in FIG. 15, or at an angle to the longitudinal axis of the probe. In use, the light illuminates the area of interest (e.g., a pedicle) to provide the surgeon with enhanced visibility of the area as observed through the lens 25 of the endoscope 22.

Figure 16:
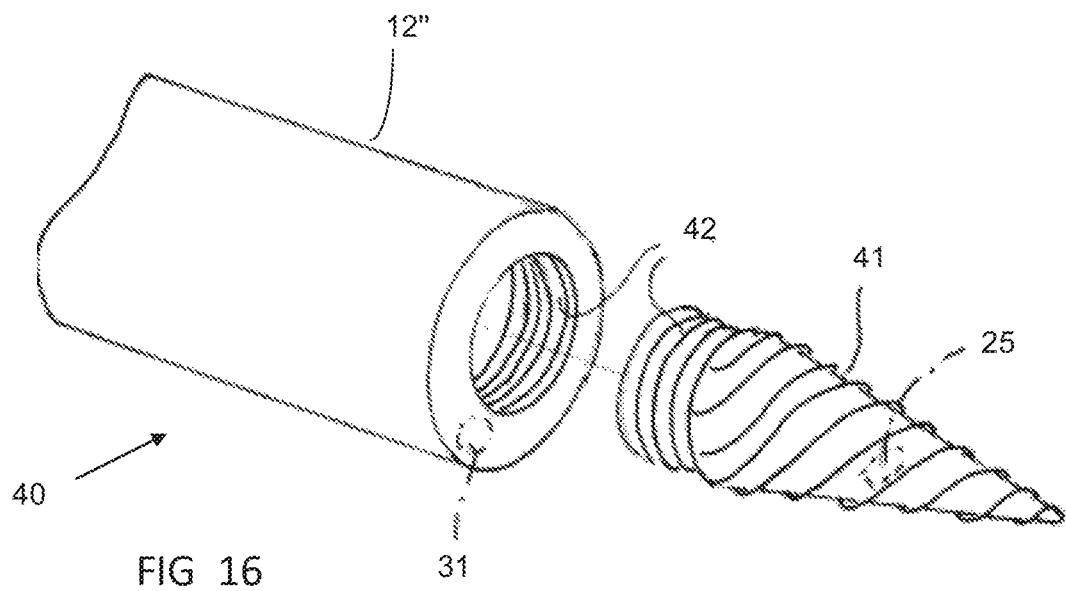
FIG. 16 is an enlarged fragmentary isometric view of the distal end of one embodiment of pedicle probe according to the invention, showing a removable tip.
Figure 17:
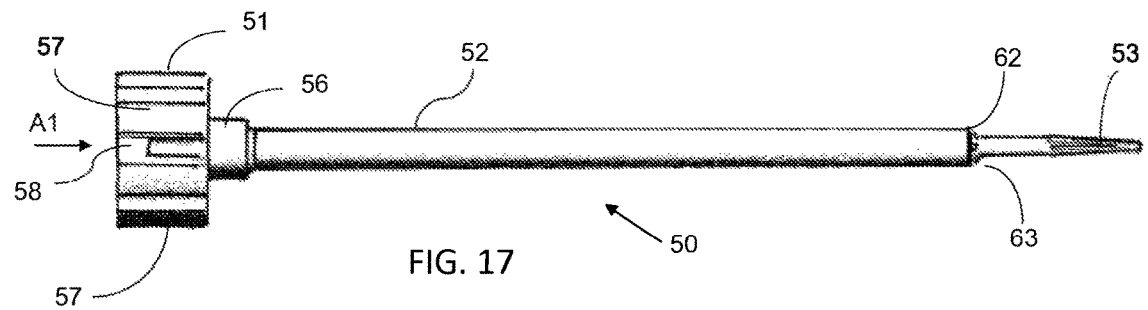
FIG. 17 is a side view in elevation of another embodiment of pedicle probe according to the invention.
Figure 18:
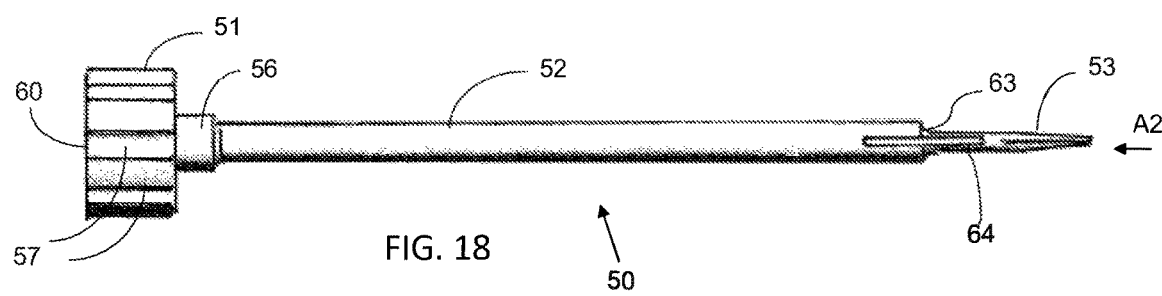
FIG. 18 is a side view in elevation of the probe of FIG. 17, taken at 90° to the view in FIG. 17.
Figure 19:
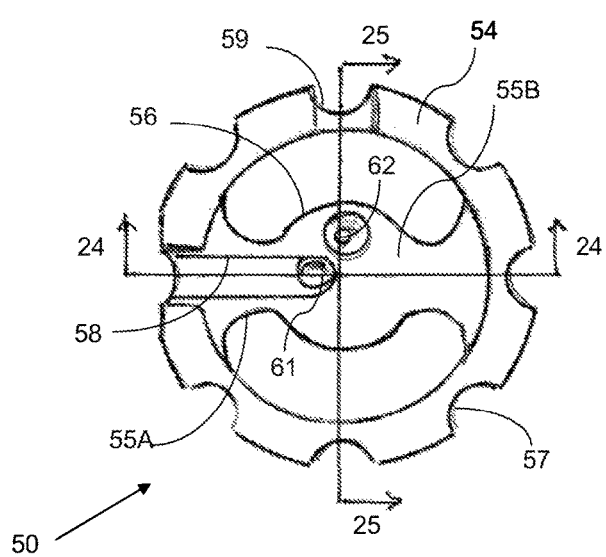
FIG. 19 is an end view of the probe of FIGS. 17 and 18, taken in the direction of the arrow 19 in FIG. 17.
Figure 20:
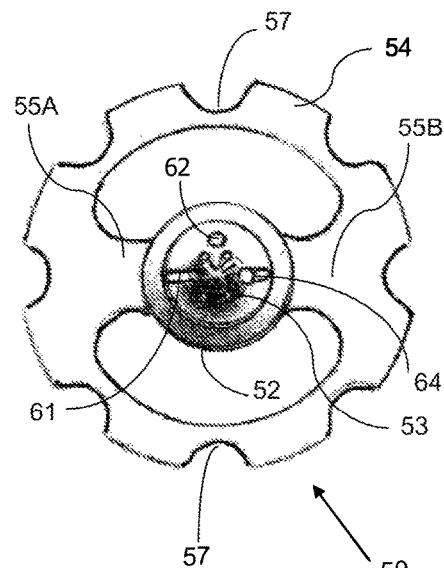
FIG. 20 is an end view of the probe of FIGS. 17 and 18, taken in the direction of the arrow 20 in FIG. 17.
Figure 21:
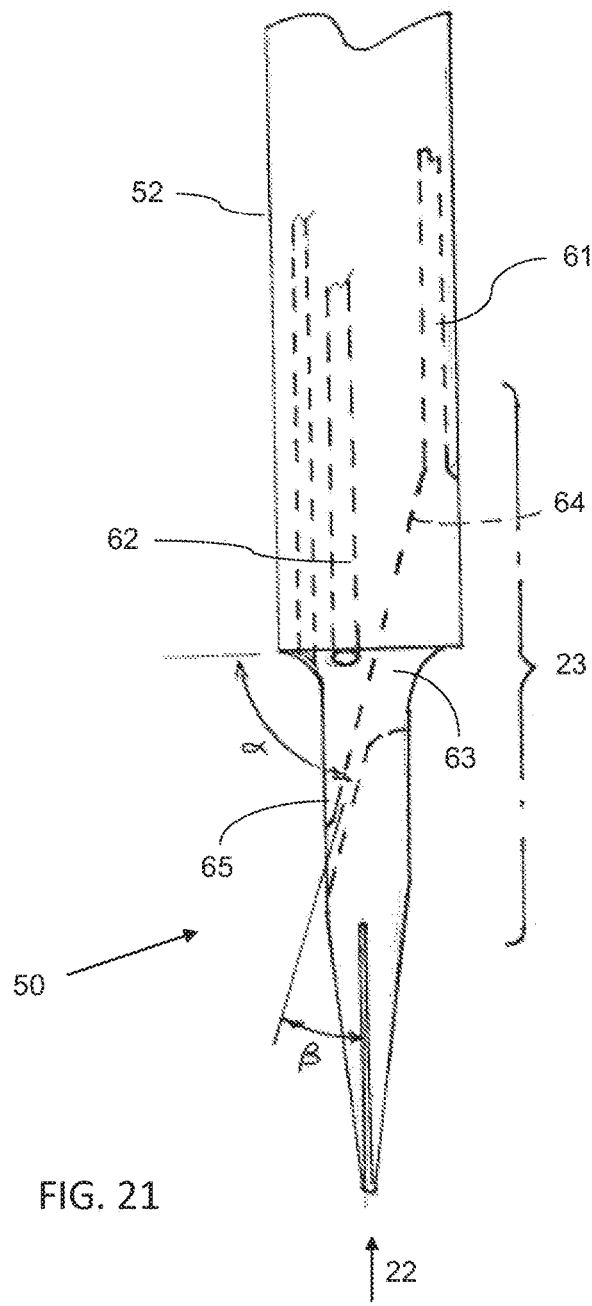
FIG. 21 is an enlarged fragmentary view in elevation of the distal end of the shaft and the tip on the distal end in the embodiment of probe shown in FIGS. 17-20.
Figure 22:
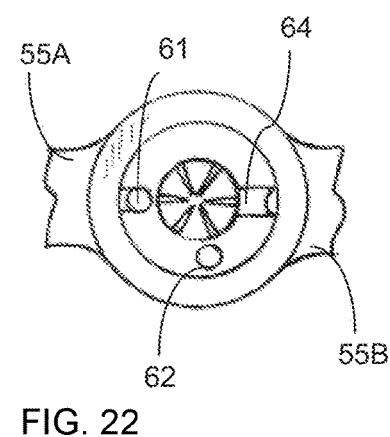
FIG. 22 is a further enlarged fragmentary end view of the probe of FIG. 21, taken in the direction of the arrow 22 in FIG. 21.
Figure 23:
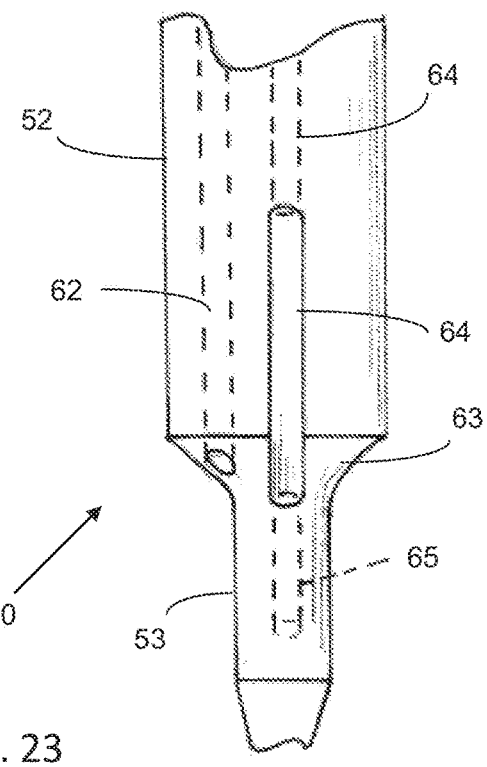
FIG. 23 is a slightly enlarged fragmentary side view in elevation of the area indicated generally by the bracket 23 in FIG. 21.
Figure 24:
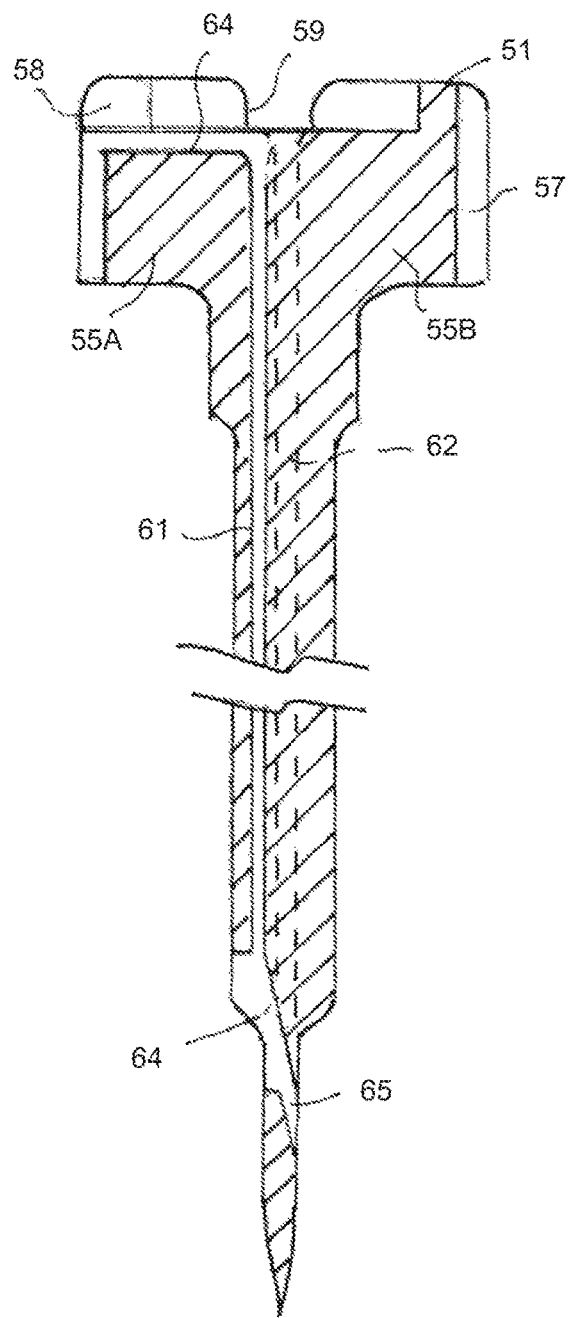
FIG. 24 is a sectional view taken along line 24-24 in FIG. 19.
Figure 25:
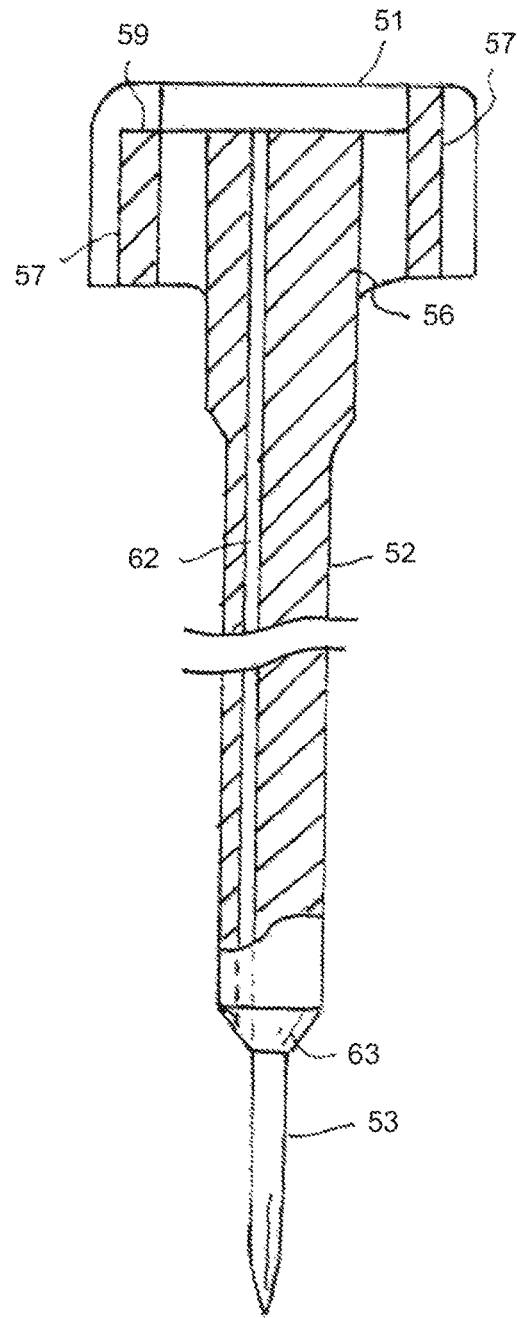
FIG. 25 is a sectional view taken along line 25-25 in FIG. 19.

FIG. 16 depicts a third embodiment 40 of pedicle probe in which the tip 41 is removable. In the example shown the removable tip has a threaded connection 42 with the shaft 12", but other means (not shown) of securely removably attaching the tip 41 to the shaft could be utilized. The removable tip may be made of any suitable material, including carbon fiber, and enables tips with different designs to be used on the probe and also enables the tip to be replaced if it becomes worn or damaged during use, thereby avoiding the necessity of having to replace or dispose of the entire probe. The removable tip may be used without either the lens of FIGS. 3-6 or the light of FIG. 15, or it may be used in combination with either or both the endoscope and light, shown as optional features in broken lines at 25 and 31 in FIG. 16. In those instances where a functional tip is not needed, a cap, passive tip, or the like could be used.

Figure 7:
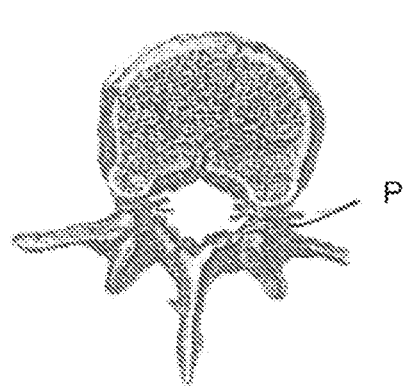
FIG. 7 is an axial view of a pedicle.
Figure 8:
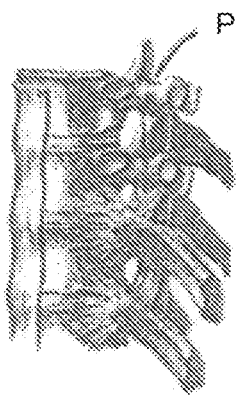
FIG. 8 is a sagittal view of a pedicle.
Figure 9:
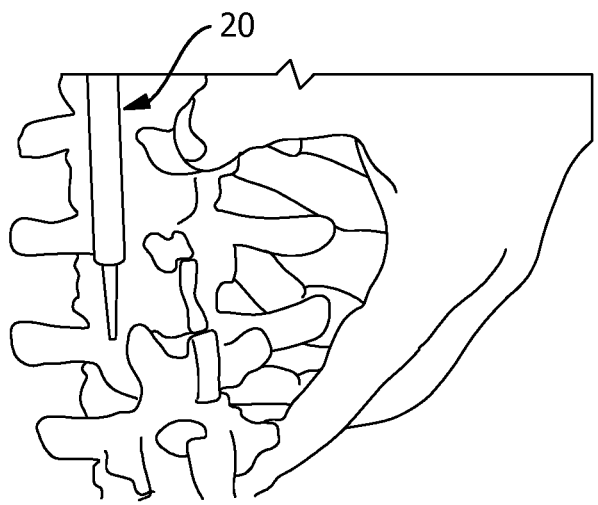
FIGS. 9 and 10 are fragmentary perspective views depicting how a pedicle probe is used to form a hole in a pedicle.
Figure 10:
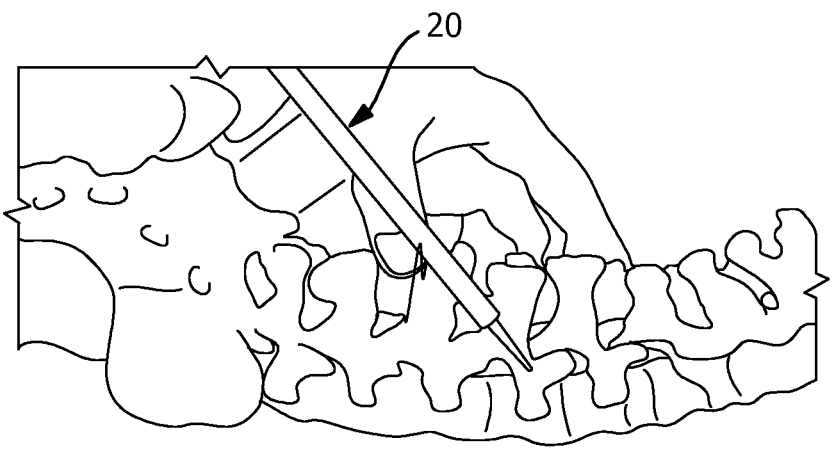
Figure 11:
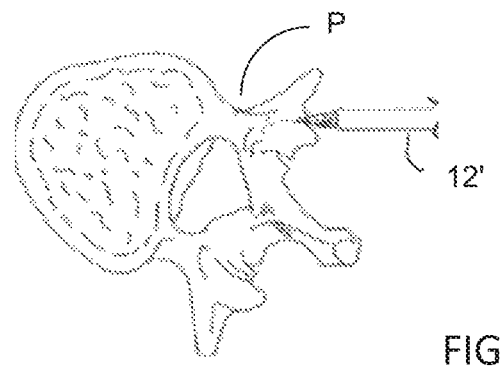
FIGS. 11-14 are somewhat schematic views depicting the progressive steps in forming a hole in the pedicle using the pedicle probe.
Figure 12:
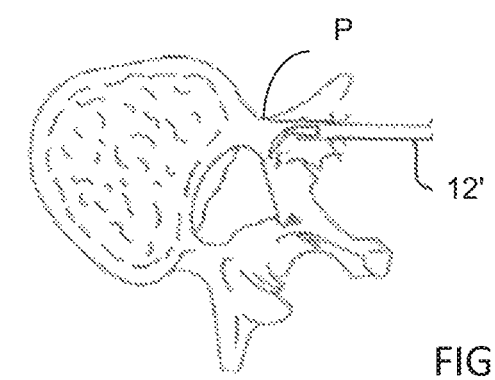
Figure 13:
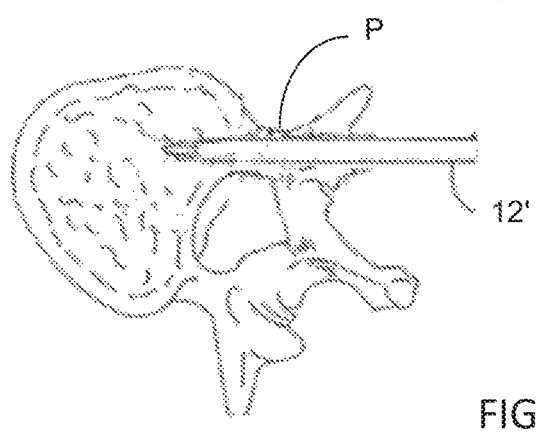
Figure 14:
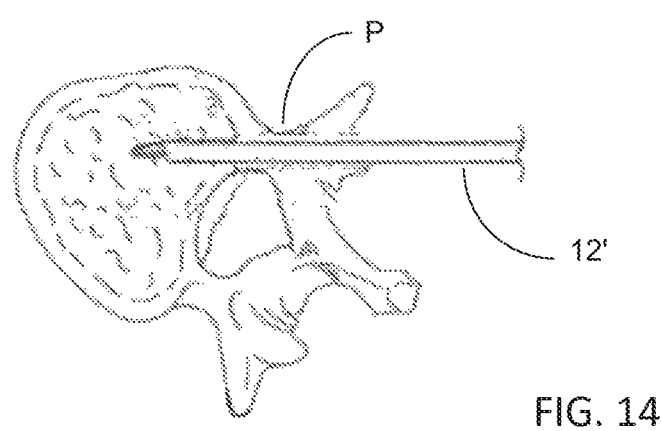

FIGS. 7 and 8 are axial and sagittal views, respectively, of a pedicle P, and FIGS. 9-14 are schematic illustrations of how a probe 20 might be used to form a hole in the pedicle. Thus, and as seen especially in FIGS. 10-14, the probe is pushed through the pedicle to form a hole for reception of a pedicle screw (not shown). Depending upon the structure of the tip 13' the probe also may be rotated back and forth to assist in forming the hole. Great care must be exercised to ensure that the probe stays within the pedicle and does not break through the wall, or does not go too deep.

A fourth embodiment 50 of pedicle probe according to the invention is shown in FIGS. 17-25. The probe 50 has an enlarged generally disc-shaped head 51 on its proximal end for grasping by the surgeon as in the previous embodiments, an elongate reduced diameter shaft 52 projecting from the center of one side of the head, and a further reduced diameter tip 53 extending coaxially from the distal end of the shaft. The head comprises a circumferential rim 54 connected to the proximal end of the shaft 52 by at least two spokes 55A and 55B that join the rim with a hub 56 on the proximal end of the shaft. The outer surface of the rim is longitudinally fluted at 57, and two circumferentially spaced recesses 58 and 59 are formed in the upwardly facing proximal end surface 60 of the rim. As used herein, "upwardly facing" refers to the orientation when the probe is in its operative position during use. In the particular construction shown, the recesses are in alignment with respective flutes 57 and are circumferentially spaced apart 90°. Two bores 61 and 62 are formed longitudinally through the hub and shaft in positions oriented respectively on a radius extending through a respective recess 58 or 59. One of the bores 62 exits the distal end of the shaft in an axially forwardly facing shoulder 63 between the base end of the tip 53 and the adjacent end of the shaft 52. The other bore 61 ends in a slot 64 formed in the side of the shaft 52 at its distal end and extending angularly at an angle β of 16° relative to the longitudinal axis of the shaft 52 into the base end of the tip 53. A bore 65 extends from the slot 64 and diagonally through the tip 53 to exit an opposite side of the tip, providing a view extending over an angle α of 74°.

Figure 26:
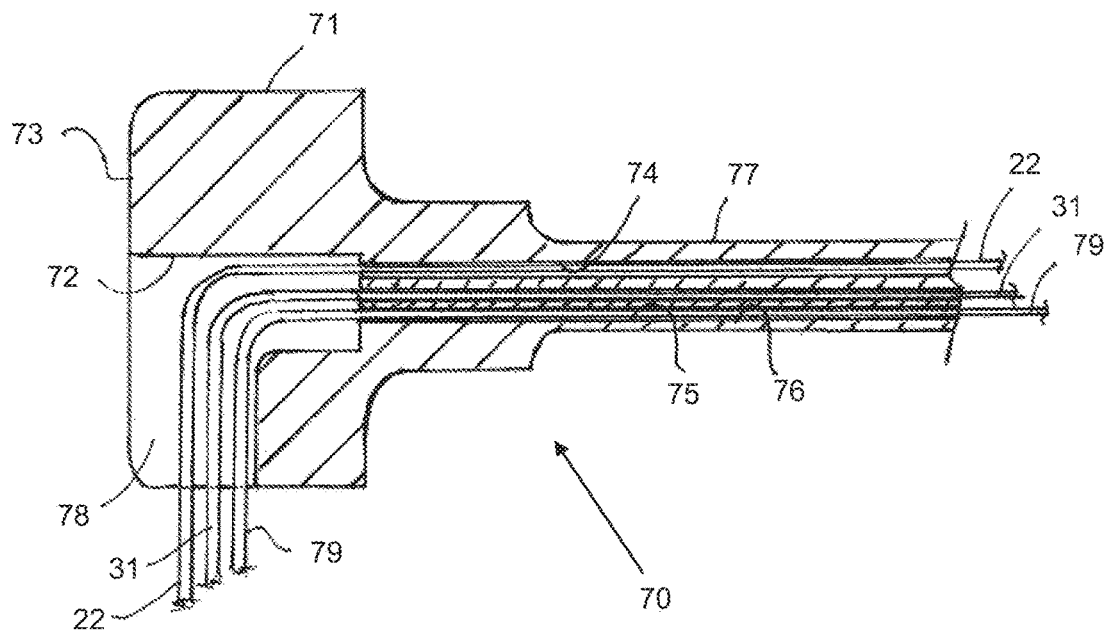
FIG. 26 is a fragmentary longitudinal sectional view of another embodiment of pedicle probe according to the invention.
Figure 27:
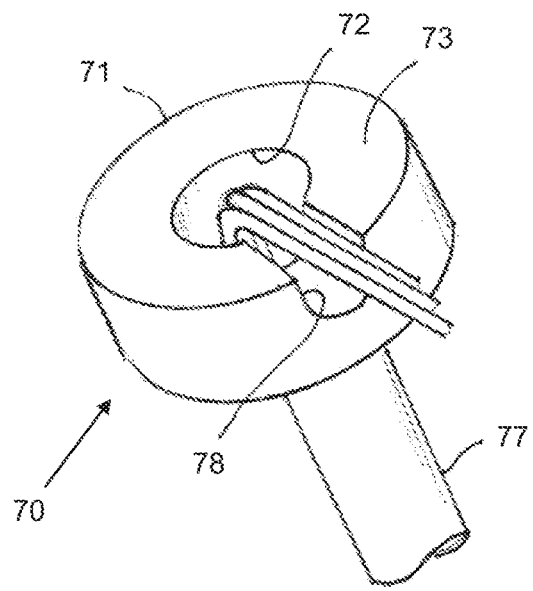
FIG. 27 is a fragmentary top isometric view of the probe of FIG. 26.
Figure 28:
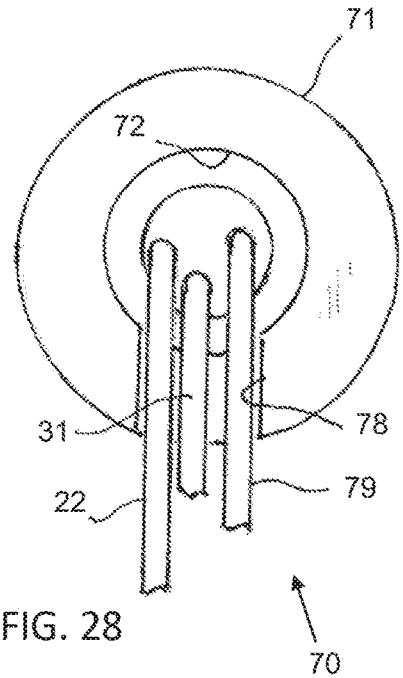
FIG. 28 is an end view in elevation of the probe of FIG. 26, looking from the left hand side of FIG. 26.
Figure 29:
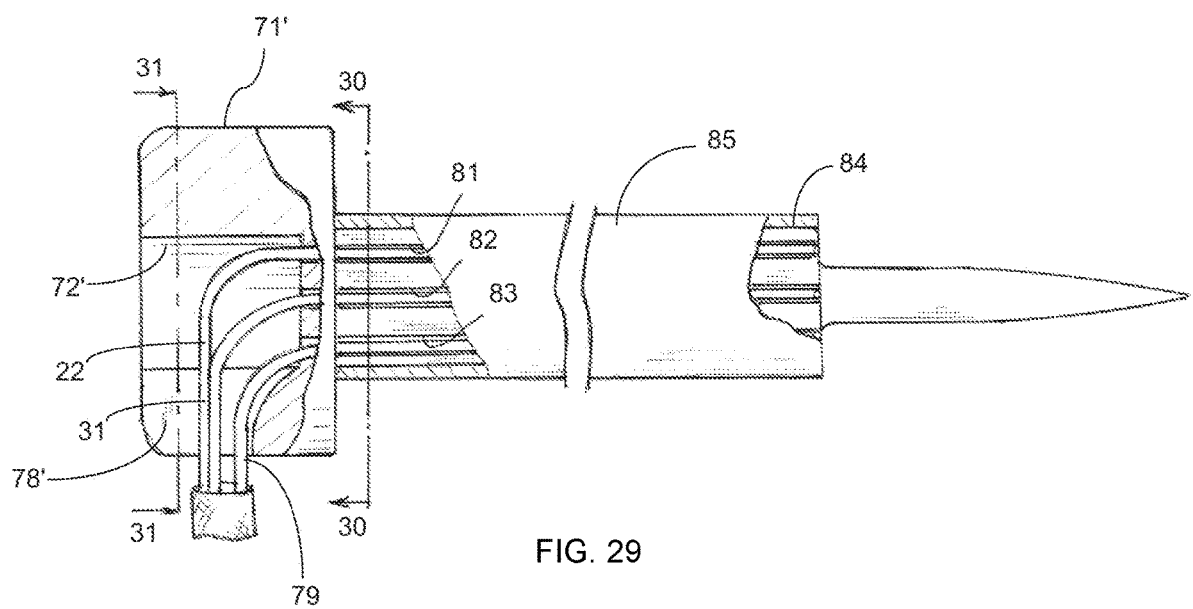
FIG. 29 is a side view, shown partially in section and partially in elevation, of a further modified probe according to the invention, wherein channels are formed in the outer surface of the probe shaft and feeds for the light, camera and flushing liquid are placed in these channels, with a surrounding sleeve placed over the shaft to secure the parts in place.
Figure 30:
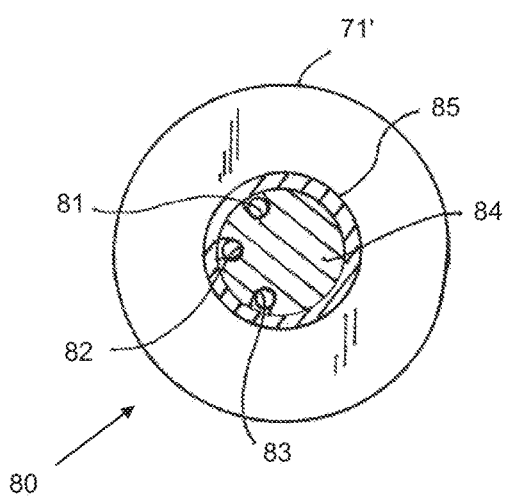
FIG. 30 is a transverse sectional view taken long line 30-30 in FIG. 29.
Figure 31:
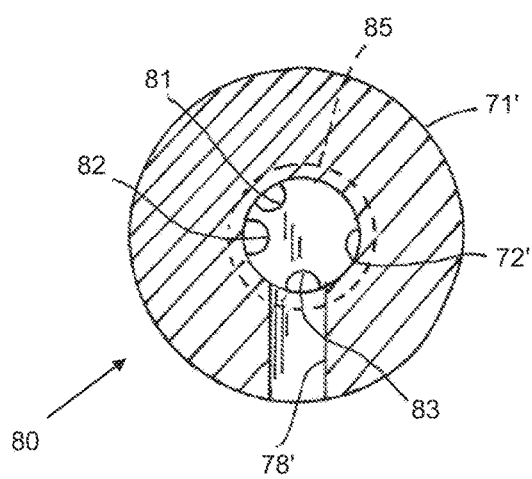
FIG. 31 is a transverse sectional view taken long line 31-31 in FIG. 29.
Figure 32:
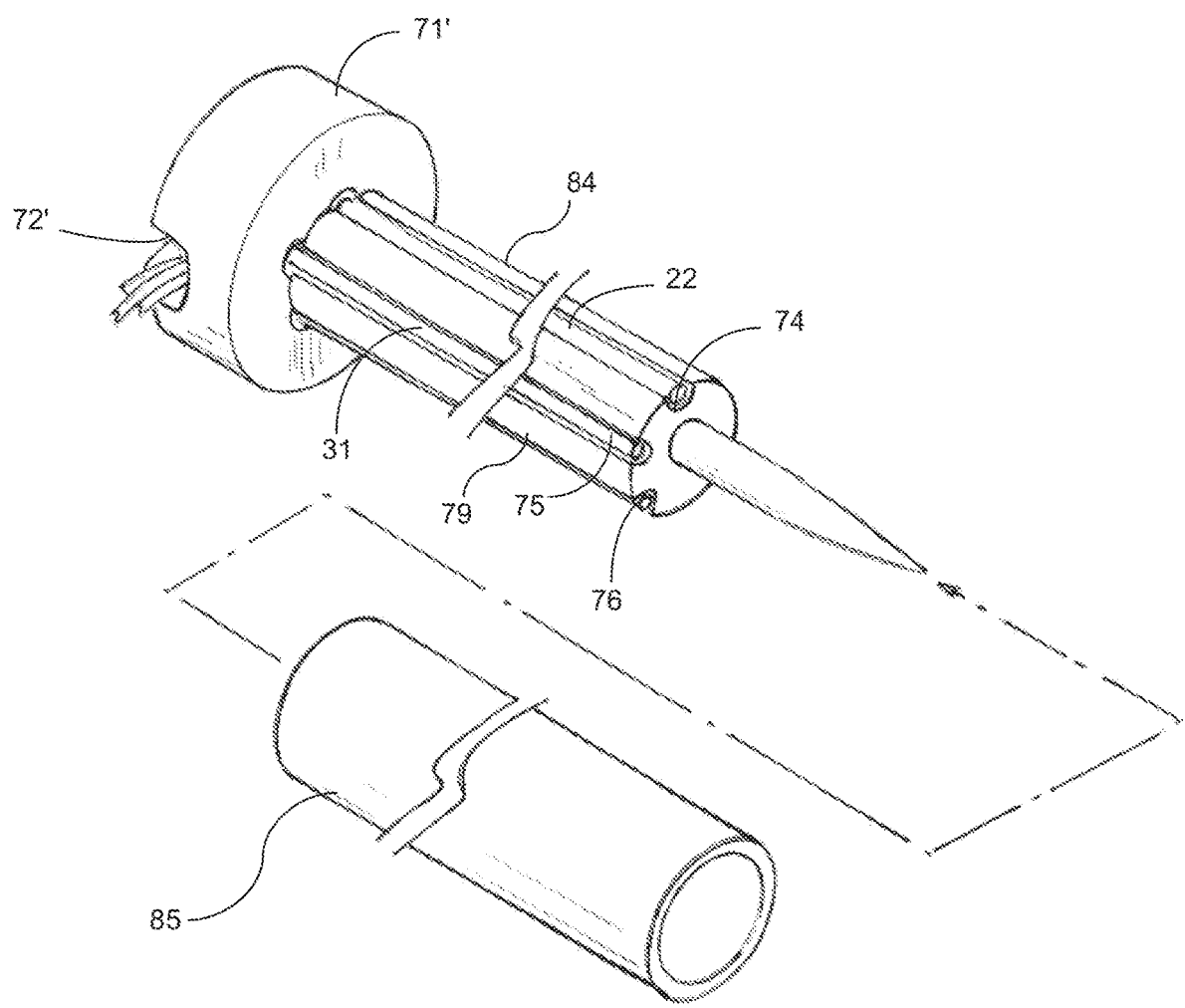
FIG. 32 is an exploded isometric view, with portions broken away, of the probe and sleeve of FIGS. 29-31.

A fifth embodiment 70 of pedicle probe according to the invention is shown in FIGS. 26-28. In this embodiment, the proximal end or head 71 of the probe has a central opening 72 extending inwardly from its axially upwardly facing surface 73, and a plurality of bores 74, 75, and 76 extend longitudinally through the shaft 77 from the base of the opening. A radial notch 78 in the axially upwardly facing surface connects the central opening with the outer circumference of the head. An endoscope 22, light 31, and conduit 79 for conveying a flushing fluid to the distal end of the probe to remove body fluids and debris from the area being worked on extend through the notch 78 and through the bores 74, 75, and 76, respectively. Although not shown in FIGS. 26-28, the bores 74, 75, and 76 could exit through the shoulder between the base end of the tip and the distal end of the shaft (see, e.g., shoulder 63 in FIGS. 24 and 25), or the endoscope bore could terminate in a slot such as slot 64 seen in FIGS. 21-23. Also, as not shown in FIGS. 26-28, the tip could be integrally formed with the shaft as seen in FIGS. 17-25 or it could be detachable as seen in FIG. 16.

A sixth embodiment 80 of pedicle probe according to the invention is shown in FIGS. 29-32. In this form of the invention, rather than extend bores longitudinally through the body of the shaft for containing the endoscope, light, and conduit for the flushing fluid, longitudinally extending channels 81, 82, and 83 are formed in the outer surface of the shaft 84, and a cylindrical sleeve 85 is positioned in snug relationship over the shaft in an enclosing relationship to the channels and the endoscope 22, light 31, and conduit 79 held therein. As in the previous embodiments, the tip may be integral with the shaft or detachable. Similarly to the embodiment shown in FIGS. 26-28, the head 71' has a central opening 72', and the endoscope 22, light 31, and flushing conduit 79 are fed through a notch 78' in the end surface of the head.

Figure 33:
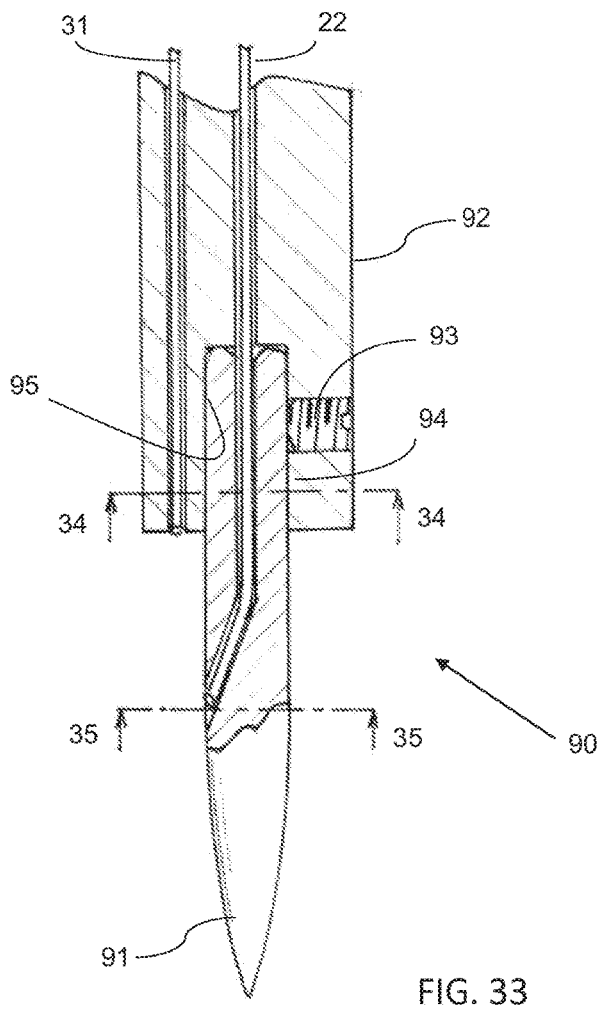
FIG. 33 is a fragmentary enlarged sectional view of the distal end of a further embodiment of the invention wherein a removable tip is held in place by a set screw and is aligned in proper position by a keyway.
Figure 34:
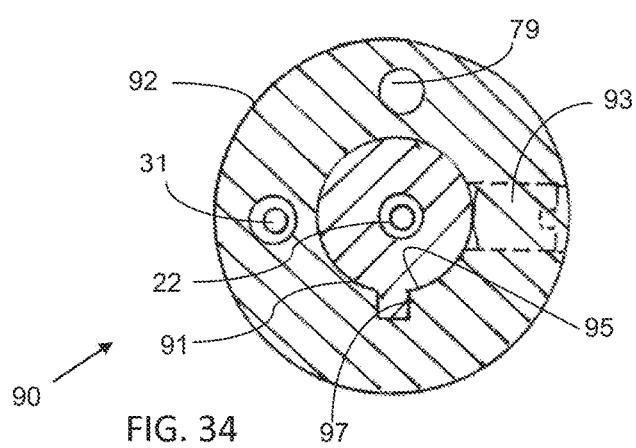
FIG. 34 is a transverse view in section taken along line 34-34 in FIG. 33.
Figure 35:
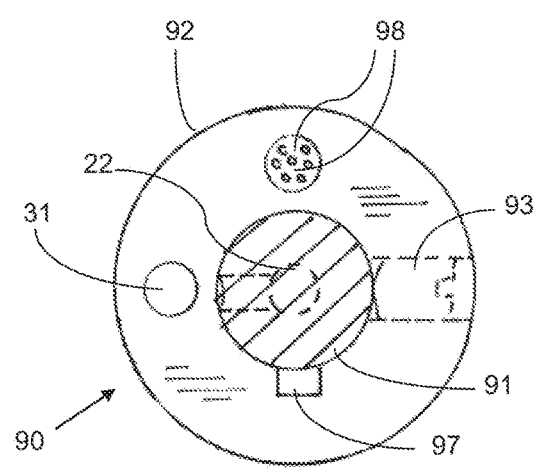
FIG. 35 is a transverse view in section taken along line 35-35 in FIG. 33.

A seventh embodiment 90 of pedicle probe according to the invention is shown in FIGS. 33-35. In this form of the invention, the tip 91 is detachably secured to the distal end of the shaft 92 by a set screw 93 extended through the side of the shaft and into engagement with the base end 94 of the tip 91, which is inserted into an axial bore 95 in the distal end of the shaft. Proper rotational positioning of the tip relative to the shaft is achieved by a keyway formed by an axially extending groove or slot in the interior surface of bore 95 and a complementarily shaped key 97 on the exterior of the base end 94 of the tip 91. The tip 91 may be readily detached from the shaft 92 by loosening the set screw 93 and may be used with any of the previous forms of the invention. An endoscope 22 and/or a light 31 and/or a conduit 79 for flushing fluid, all shown in FIGS. 33-35, may be used in combination with the detachable tip, or the detachable tip may be used without any of these. As seen in FIG. 35, the outlet for the flushing fluid may have numerous small orifices 98 to provide a "soft" flow of flushing fluid against the area being treated.

Figure 37:
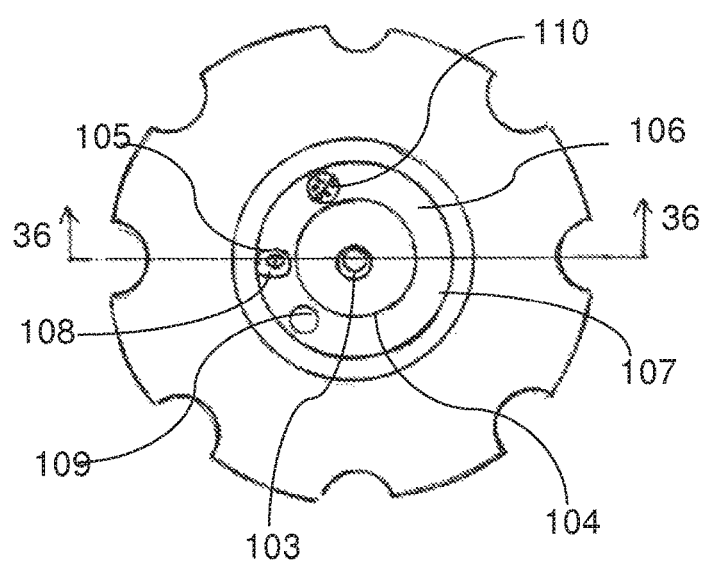
FIG. 37 is an enlarged end view looking in the direction of the arrow "37" in FIG. 36.
Figure 36:
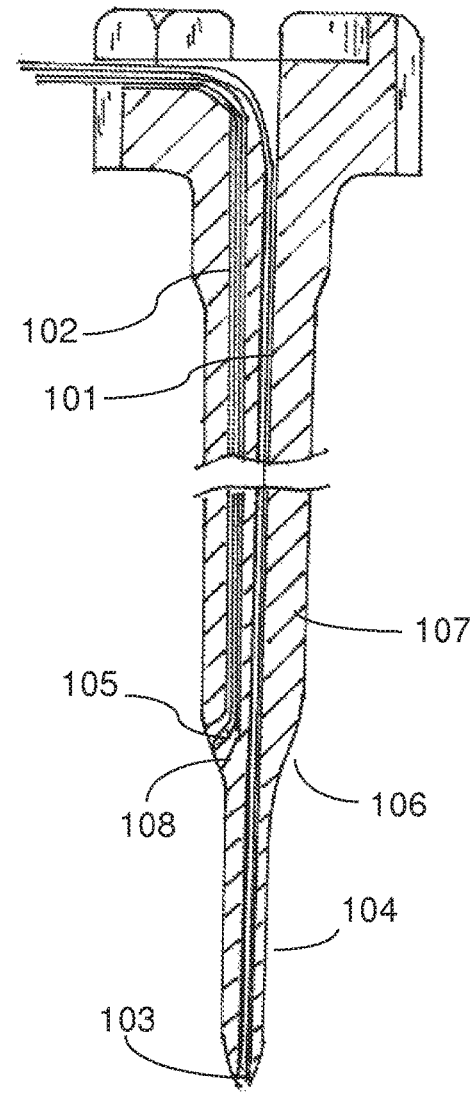
FIG. 36 is a longitudinal sectional view of a further embodiment of the invention, taken along line 36-36 in FIG. 37, wherein two endoscopes are associated with the probe, and a light means and saline flush means are provided for illuminating the area being treated and for flushing away debris to maintain a clear field of view.

An eighth embodiment 100 of probe according to the invention is shown in FIGS. 36 and 37. In this embodiment, two endoscopes 101 and 102 are provided in the probe. One of the endoscopes 101 has its camera 103 positioned at the distal end of the tip 104 in a 0° forwardly facing orientation. The other endoscope 102 has its camera 105 positioned at the distal end 106 of the probe shaft 107 and oriented in a camera window slot 108 to provide about a 70° view looking at the side of the pedicle wall. A bright fiber optic light source 109 is positioned at the distal end of the probe shaft adjacent the window 108 for the camera 105. The light illuminates the pedicle and surrounding bony structures which will give visualization within the cancellous portion of the pedicle. A saline rinse port 110 is also preferably provided at the distal end of the probe shaft to rinse away debris during use of the probe to keep the field of vision clear.

One example of a suitable endoscopic camera for use in the probe of the invention is the 1.2 mm micro camera available from Medigus, Ltd. of Omer, Israel. This camera has a diameter of only 1.2 mm and a length of only 5 mm. It has high quality 100° FOV optics and a shielded camera cable with a metal connector as well as a video processor.

In a typical example of a probe made in accordance with the invention, the shaft can have a length of about 28 cm and a diameter of from about 6 mm to about 12 mm; the tip can have a length of about 40 mm and a diameter of from 4 to about 5 mm; and the endoscope 22, light 32, and conduit 79 for flushing fluid each can have a diameter of from about 1 mm to about 2 mm. In those embodiments wherein the camera for the endoscope is located adjacent the proximal end of the tip, it can be placed along the tip a distance spaced approximately 6 to 8 mm from where the tip is joined to the end of the shaft, and preferably is oriented at an angle of 45° to 90° relative to the longitudinal axis of the tip. It should be noted that these are exemplary dimensions only and the probe and its components could have other dimensions as necessary or desirable.

The endoscopic probe of the invention provides the surgeon with an illuminated, direct visual indication of the exact location of the probe and provides for flushing body fluids and debris away from the area being treated, whereby the hole can be formed with accuracy and precision.

While particular embodiments of the invention have been illustrated and described in detail herein, it should be understood that various changes and modifications may be made to the invention without departing from the spirit and intent of the invention as defined by the scope of the appended claims. For example, while the general inventive concepts have been shown and described in the context of a pedicle probe, the general inventive concepts encompass other probes which may have different functional tips and, in some cases, no functional tip.

What is claimed is:

1. A probe for performing a surgical procedure, the probe comprising:
   an enlarged proximal end for cooperation with the hand of a surgeon using the probe to aid in controlling the probe;
   an elongate shaft having a longitudinal axis and extending from the enlarged proximal end and terminating in a distal end;
   a detachable shaped tip on the distal end of the shaft, the tip having a reduced diameter relative to the shaft;
   a bore extending longitudinally through the shaft and an endoscope extending through the bore, the endoscope including a camera having a lens positioned to provide a view of an area being treated and the endoscope being connected with an external monitor for conveying a visual image of the position of the tip relative to the area being treated during the surgical procedure, whereby the surgeon is provided with direct visual indication of the exact position of the probe during the surgical procedure;
   the lens being positioned rearwardly of the distal point of the tip, whereby the lens is protected as the probe is inserted into a hard, bony material; and
   wherein the detachable tip enables a damaged or worn tip to be replaced, or a tip with different characteristics to be employed, without replacing the entire probe.

2. The probe of claim 1, wherein a second bore extends longitudinally through the shaft, the second bore exiting the shaft at about the same distance from the tip of the probe as the lens, and a light is associated with the second bore to illuminate the area being treated.

3. The probe of claim 1, wherein the tip has flutes like a drill bit, and the lens and an opening for receipt of the lens are positioned in the base of a channel formed between the flutes.

4. The probe of claim 1, wherein the lens is oriented to provide a view at 90° relative to the longitudinal axis of the shaft.

5. The probe of claim 1, wherein the lens is oriented to provide a forward view at 45° relative to the longitudinal axis of the shaft.

6. The probe of claim 1, wherein the lens is oriented to provide a straight-ahead forward view relative to the longitudinal axis of the shaft.

7. The probe of claim 1, wherein the surgical procedure requires the formation of a hole in a hard, bony material of the spine of a patient; and
   the tip has a hardness and configuration adapted to be pushed through the hard, bony material to form a hole.

8. The probe of claim 2, wherein a third bore extends longitudinally through the shaft, the third bore exiting the shaft at about the same distance from the distal end of the probe as the lens; and a conduit for a fluid to flush the area being treated extends through the bore to flush body fluid and debris away from the area being treated.

9. The probe of claim 1, wherein the detachable tip is threadably attached to the shaft.

10. The probe of claim 1, wherein a coaxial bore in the base end of the tip is in axial alignment with the first bore in the shaft, and the coaxial bore in the base end of the tip connects with an angularly extending diagonal bore opening through a side of the tip, the first camera being positioned in the diagonal bore where it exits through the side of the tip.

11. The probe of claim 10, wherein the second and fourth bores open through the distal end of the shaft in rotationally spaced relationship to one another, the tip being rotationally oriented relative to the shaft so that the light is positioned on the same side of the probe as the diagonal bore and the camera.

12. The probe of claim 11, wherein a keyway is formed between the base end of the tip and the coaxial bore in the shaft to rotationally orient the tip when it is attached to the shaft so that the light is positioned on the same side of the probe as the diagonal bore and the camera.

13. A probe for performing a surgical procedure, the probe comprising:
   an enlarged proximal end forming a head for cooperation with the hand of a surgeon using the probe to aid in controlling the probe;
   an elongate shaft having a longitudinal axis and extending from the enlarged proximal end and terminating in a distal end;
   a reduced diameter tip on the distal end;
   a longitudinally extending channel formed in an outer surface of the shaft;
   an endoscope extending through the head and through the at least one channel, the endoscope including a camera at the distal end of the shaft; and
   a cylindrical sleeve telescoped over the shaft and over the at least one channel and endoscope positioned therein.

14. The probe of claim 13, wherein a second longitudinally extending channel is formed in the outer surface of the shaft, the second channel exiting the shaft rearwardly of the distal end of the shaft, and a light means extends through the head and through the second channel to illuminate an area viewed by the endoscope.

15. The probe of claim 14, wherein a third longitudinally extending channel is formed in the outer surface of the shaft, the third channel exiting the shaft rearwardly of the distal end of the shaft at about the same distance as the second channel exit, and a conduit extends through the third channel for conveying a fluid to an area being treated to flush body fluid and debris away from the area.

16. The probe of claim 13, wherein the tip has a hardness and configuration adapted to be pushed through a hard, bony structure to form a hole.

* * * * *